US005256805A

United States Patent [19]

O'Lenick, Jr.

[11] Patent Number: 5,256,805

[45] Date of Patent: Oct. 26, 1993

[54] SILICONE AMIDO AMINE SALTS

[75] Inventor: Anthony J. O'Lenick, Jr., Lilburn, Ga.

[73] Assignee: Siltech Inc., Norcross, Ga.

[21] Appl. No.: 981,531

[22] Filed: Nov. 25, 1992

[51] Int. Cl.[5] .......... C07F 7/10

[52] U.S. Cl. .......... 554/39; 556/419

[58] Field of Search .......... 556/419; 554/39

[56] References Cited

U.S. PATENT DOCUMENTS

| | | | |
|---|---|---|---|
| 4,104,296 | 8/1978 | Pike | 556/419 |
| 4,548,842 | 10/1985 | Pohl | 554/39 X |
| 4,844,888 | 7/1989 | Zawadzki | 429/69 |
| 4,891,166 | 1/1990 | Schaefer et al. | 554/39 |
| 4,973,643 | 11/1990 | O'Lenick, Jr. | 528/15 |
| 5,070,168 | 12/1991 | O'Lenick, Jr. | 528/10 |
| 5,115,049 | 5/1992 | Imperante et al. | 556/419 X |

Primary Examiner—Paul F. Shaver

[57] ABSTRACT

The invention relates to a series of novel silicone amido amine salts, an amido amine intermediate and a process for their preparation. This class of compounds are prepared by the reaction of a carboxy silicone and dimethylaminopropyl amine followed by the neutralization reaction of the amine with an acid selected from the group consisting of acetic, lactic, and fatty acids having from 6 to 44 carbon atoms. The products surface active agents which by selection of the proper neutralization acid can be used for the preparation of water in oil or oil in water emulsions.

17 Claims, No Drawings

SILICONE AMIDO AMINE SALTS

BACKGROUND OF THE INVENTION

1. Field of the Invention

The invention relates to a series of novel silicone amido amine salts, an amido amine intermediate and a process for their preparation. This class of compounds are prepared by the reaction of a carboxy silicone and dimethylaminopropyl amine followed by the neutralization reaction of the amine with an acid selected from the group consisting of acetic, lactic, and fatty acids having from 6 to 44 carbon atoms. The products surface active agents which by selection of the proper neutralization acid can be used for the preparation of water in oil or oil in water emulsions.

2. Arts and Practices

Silicone compounds have been known to be active at the surface of cellulosic and synthetic fibers as well as paper. They are good nondurable lubricants and are very stable to oxidation, however, their high cost and lack of efficiency at low concentrations as well as low durability have made their acceptance in commercial products quite low.

In addition to their high cost, silicone compounds have little or no solubility in mineral oils, fatty triglycerides and other classical fatty quaternary compounds used for softening. This has resulted in the inability to prepare stable blends for use as a textile fiber treatment.

In many applications, there is a desire for a more fatty soluble softener. The desired molecule should have the desirable softening and antistatic properties of silicone, yet have compatability with traditional fatty materials and oils. Even though a textile softener which has both the desirable softening and antistatic properties of silicone as well as compatibility with fatty compounds has been a long felt need, it isn't until the compounds of the present invention that such a system has been attained.

Carboxy containing silicone compounds useful as raw materials in the practice of the present invention are known to those skilled in the art. U.S. Pat. No. 4,844,888 issued in 1989 to Zawadizki discloses the carboxy containing silicone compounds useful as raw materials in the preparation of the compounds of the present invention.

U.S. Pat. No. 4,973,643 to O'Lenick, Jr. teaches that silicone ether amines can be prepared by cyanoethylation of dimethicone copolyols. These materials are non-amido containing amines.

U.S. Pat. No. 5,070,168 to O'Lenick, Jr. teaches a process for using the compounds covered by U.S. Pat. No. 4,973,643 for conditioning fiber.

THE INVENTION

Object of the Invention

It is the object of the present invention to provide novel series of silicone amido amine salts. These compounds are surface active and can be used to produce very stable oil in water or water in oil emulsions, depending upon the carboxy silicone and the neutralizing acid chosen.

It is an additional object of the present invention to provide an silicone amido amine compound which is useful as an intermediate in the preparation of the compounds of the present invention.

It is another objective of the current invention to provide a novel process for the preparation of silicone amido amine compounds.

SUMMARY OF THE INVENTION

One aspect of the present invention relates to a series of novel silicone amido amine intermediates.

Another aspect of the present invention relates to a series of novel silicone betaines. These compounds by virtue of the amide group and positive charge on the nitrogen, form unique emulsions of the water in oil or oil in water type depending upon the exact carboxy silicone and the exact neutralizing acid chosen. When lower acids are chosen, like lactic or acetic, the products so formed tend to form oil in water emulsions. When fatty acids are chosen for neutralization, the resulting salts are soluble in fatty and hydrocarbon products, and give water in oil emulsions.

The intermediate amido amine compounds of the present invention conform to the following structure;

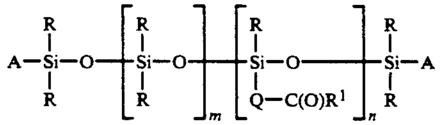

Wherein

R is methyl;

$R^1$ is $N(H)—(CH_2)_3—N(CH_3)_2$

Q is $—(CH_2)_a—$ a is an integer ranging from 3 to 17;

A is either —R or $—Q—C(O)—R^1$, m is an integer ranging from 1 to 200;

n is an integer ranging from 1 to 10.

$R^4$ is H or $CH_3$.

The compounds of the present invention are prepared by the reaction of a carboxy silicone with an dimethylaminopropyl amine, which conforms to the following structure;

$H_2N—(CH_2)_3—N(CH_3)_2$

The process used for the preparation of the intermediate compounds of the present invention comprises the amidification reaction of (a) a carboxy containing silicone compound conforming to the following structure;

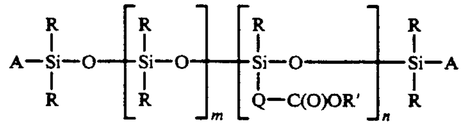

Wherein

R is methyl;

R' is hydrogen;

Q is $(CH_2)_c$;

c is an integer from 3 to 17;

A is selected from the group consisting of methyl and $—Q—C(O))R'$;

with (b) dimethylaminopropyl amine said amidification reaction to be carried out by mixing said carboxy silicone and said dimethylaminopropyl amine and heating said mixture to a temperature of between 120 and 250 C. for between 1 and 15 hours. Water is distilled off.

PREFERRED EMBODIMENTS

In a preferred embodiment, the temperature of the reaction ranges from 150 to 200 C.

In a still more preferred embodiment the temperature ranges from 150 to 180 C.

EXAMPLES OF AMIDOAMINE INTERMEDIATE

The compounds of the present invention are prepared by the reaction of a carboxy silicone compound and an dimethylaminopropyl amine. Examples of suitable reactants are as follows;

REACTANTS

Carboxy Silicone Compounds

Many manufactures offer a series of carboxy functional silicone compounds suitable for use as raw materials in the preparation of the esters of the present invention. These materials are marketed under the many trade names. Two companies making them are Siltech Inc, and Dow Corning.

The preferred method of placing this type of reactive carboxy group into the silicone polymer is by the reaction of silanic hydrogen containing polymer with a terminal unsaturated carboxylate. This technology is well known to those skilled in the art.

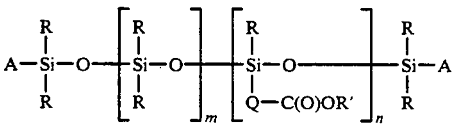

wherein
R is methyl;
R' is hydrogen;
Q is $(CH_2)_c$;
c is an integer from 3 to 17;
A is methyl;

| Example | Name | c | n | m |
|---|---|---|---|---|
| 1 | Siltech C 1000 | 10 | 3 | 15 |
| 2 | Siltech C 1100 | 10 | 1 | 20 |
| 3 | Siltech C 1200 | 3 | 4 | 50 |
| 4 | Siltech C 1300 | 3 | 2 | 200 |
| 5 | Siltech C 1400 | 4 | 1 | 29 |
| 6 | Siltech C 1500 | 17 | 3 | 1 |
| 7 | Siltech C 1800 | 17 | 4 | 150 |
| 8 | Siltech C 1700 | 4 | 10 | 55 |

Terminal Substituted Carboxy Silicone

Terminal substituted carboxy silicone compounds are well known and are marketed in the trade under many names.

The preferred method of placing this type of carboxyl group into the silicone polymer is by the reaction of terminal silanic hydrogen containing polymer with a terminal vinyl containing carboxy compound.

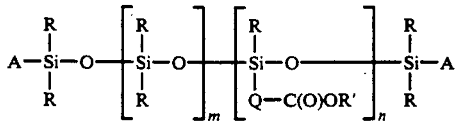

Wherein
R is methyl;
R' is hydrogen;
Q is $(CH_2)_c$;
c is an integer from 3 to 17;
n is 0;
A is —Q—C(O)OR'

| Example | Name | c | m |
|---|---|---|---|
| 9 | Siltech CT 701 | 10 | 1 |
| 10 | Siltech CT 708 | 3 | 200 |
| 11 | Siltech CT 710 | 17 | 50 |
| 12 | Siltech CT 750 | 10 | 100 |
| 13 | Siltech CT 790 | 3 | 150 |

General Reaction Conditions

The reaction is run with a excess of dimethylaminopropyl amine which is stripped off after the reaction is complete.

Into a suitable round bottom, three neck flask equipped with a thermometer and a nitrogen sparge is added the specified number of grams of the specified silicone compound and the specified number of grams of dimethylaminopropyl amine. The reaction mass is blanketed with nitrogen, and heated to 150–200 C. under the inert nitrogen blanket. Within four to five hours the acid value is vanishingly low. The product is stripped under vacuum at 200 C. to remove any unreacted dimethylaminopropyl amine. The final product is a clear liquid and is used without additional purification.

EXAMPLE 14

Into a suitable round bottom, three neck flask equipped with a thermometer and a nitrogen sparge is added 609.0 grams of silicone example 1 and 120.0 grams of dimethylaminopropyl amine. The reaction mass is then blanketed with nitrogen and heated to 150–200 C. This temperature is maintained for four to five hours. The acid value is vanishingly low after this period. The product is a clear liquid and is used without additional purification.

EXAMPLES 15–66

Example 14 is repeated only this time substituting the specified number of grams of the specified silicone compound as shown below;

| Example | Silicone Reactant Example | Compound Grams |
|---|---|---|
| 15 | 1 | 609.0 |
| 16 | 2 | 1827.0 |
| 17 | 3 | 1051.0 |
| 18 | 4 | 7570.0 |
| 19 | 5 | 2409.0 |
| 20 | 8 | 361.0 |
| 21 | 7 | 3100.0 |
| 22 | 8 | 524.2 |
| 23 | 9 | 290.0 |
| 24 | 10 | 7553.0 |

-continued

| Example | Silicone Reactant Example | Compound Grams |
|---|---|---|
| 28 | 11 | 2200.0 |
| 28 | 12 | 4000.0 |
| 27 | 13 | 5700.0 |

Preparation of the Amido Amine Salt

The amido amine salts conform to the following structure:

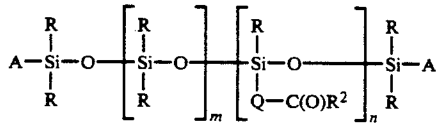

Wherein
R is methyl;
$R^2$ is

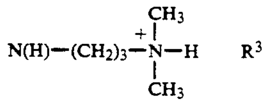

$R^3$ is $CH_3-(CH_2)_q-CH(OH)_r-C(O)-O^{\ominus}$
r is 0 or 1;
q is an integer ranging from 0 to 44;
Q is $-(CH_2)_a-$
a is an integer ranging from 3 to 17;
A is either $-R$ or $-Q-C(O)-R^1$,
m is an integer ranging from 1 to 200;
n is an integer ranging from 1 to 10.

Neutralizing Acids

Lower Acids $CH_3-(CH_2)_q-CH(OH)_r-C(O)-OH$

| Example | Name | q | r |
|---|---|---|---|
| A | Acetic | 0 | 0 |
| B | Propronic | 1 | 0 |
| C | Lactic | 0 | 1 |
| D | Glycolic | 1 | 1 |

Fatty Acids

Fatty acids which are suitable for the preparation of compounds of the present invention include the following fatty acids and mixtures thereof. The compounds conform to the following structure;

$CH_3-(CH_2)_q-CH(OH)_r-C(O)-OH$

| Example | Name | q | r |
|---|---|---|---|
| E | Caproic | 4 | 0 |
| F | Caprylic | 6 | 0 |
| G | Capric | 8 | 0 |
| H | Lauric | 10 | 0 |
| I | Myristic | 12 | 0 |
| J | Palitic | 14 | 0 |
| K | Stearic | 16 | 0 |
| L | Arachic | 18 | 0 |
| M | Hydroxy Stearic | 16 | 1 |
| N | Behenic | 20 | 0 |
| O | Lignoceric | 23 | 0 |

-continued

| Example | Name | q | r |
|---|---|---|---|
| P | Unicid TM 700 | 44 | 0 |

Unicid TM is a trademark of Petrolite Specialty Polymers Group Tulsa OK.

General Reaction Conditions

Into a suitable round bottom, three neck flask equipped with a thermometer and a nitrogen sparge is added the specified number of grams of the specified amido amine silicone compound and the specified amount of the specified neutralization. The reaction mass is heated to 70–90 C. The final product is a slightly viscous liquid and is used without additional purification.

EXAMPLE 28

Into a suitable round bottom, three neck flask equipped with a thermometer and a nitrogen sparge is added 609.0 grams of silicone amido amine example 15 and 60.0 grams of acetic acid. The reaction mass is then heated to 70–90 C. This temperature is maintained for four to five hours. The product is a slightly viscous liquid and is used without additional purification.

It can be diluted with water, glycols or other suitable solvents as desired.

| | Silicone Compound Reactant | | Neutralization Acid | |
|---|---|---|---|---|
| Example | Example | Grams | Example | Grams |
| 29 | 16 | 1827.0 | A | 60.0 |
| 30 | 17 | 1051.0 | B | 74.0 |
| 31 | 18 | 7570.0 | C | 90.0 |
| 32 | 19 | 2409.0 | D | 76.0 |
| 33 | 20 | 361.0 | A | 60.0 |
| 34 | 21 | 3100.0 | C | 90.0 |
| 35 | 22 | 524.2 | A | 60.0 |
| 36 | 23 | 290.0 | C | 90.0 |
| 37 | 24 | 7553.0 | A | 60.0 |
| 38 | 25 | 2200.0 | C | 90.0 |
| 39 | 26 | 4000.0 | A | 60.0 |
| 40 | 27 | 5700.0 | C | 90.0 |
| 41 | 16 | 1827.0 | E | 128.0 |
| 42 | 17 | 1051.0 | F | 156.0 |
| 43 | 18 | 7570.0 | G | 184.0 |
| 44 | 19 | 2409.0 | H | 212.0 |
| 45 | 20 | 361.0 | I | 240.0 |
| 46 | 21 | 3100.0 | J | 268.0 |
| 47 | 22 | 524.2 | K | 284.0 |
| 48 | 23 | 290.0 | L | 312.0 |
| 49 | 24 | 7553.0 | M | 300.0 |
| 50 | 25 | 2200.0 | N | 340.0 |
| 51 | 28 | 4000.0 | O | 382.0 |
| 52 | 27 | 5700.0 | P | 616.0 |

As can be seen from the above table the percentage of silicone relative to neutralization agent varies widely. This will dramatically alter the solubility of the salt in various solvents. It will also dramatically impact upon the emulsification properties of the salt. The more fatty component, the greater the fatty solubility. This would tend to give oil in water emulsions. Conversely, if there is more silicone than fatty, the resulting emulsifier would tend to result in water in oil emulsions. It is very useful to have available within a class of compounds, salts which could be used to make all types of emulsions.

What is claimed is:

1. A silicone amidoamine which conforms to the following structure;

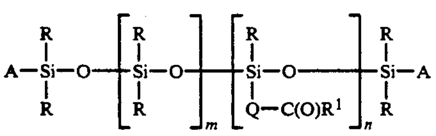

wherein

R is methyl;

$R^1$ is $N(H)-(CH_2)_3-N(CH_3)_2$

Q is $-(CH_2)_a-$;

a is an integer ranging from 3 to 17;

A is either $-R$ or $-Q-C(O)-R^1$, m is an integer ranging from 1 to 200;

n is an integer ranging from 1 to 10.

$R^4$ is H or $CH_3$.

2. A compound of claim 1 wherein

R is methyl;

R' is hydrogen;

Q is $(CH_2)_c$;

c is an integer from 3 to 17;

A is methyl.

3. A compound of claim 1 wherein

R is methyl;

R' is hydrogen;

Q is $(CH_2)_c$;

c is an integer from 3 to 17;

n is 0;

A is $-Q-C(O)-R^1$;

$R^1$ is $-N(H)-(CH_2)_3-N(CH_3)_2$.

4. A silicone amido amine salt compound which conforms to the following structure;

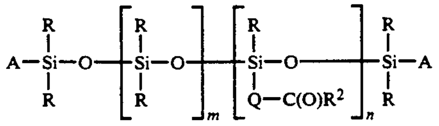

Wherein;

R is methyl;

$R^2$ is

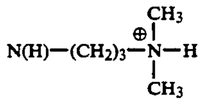 $R^3$;

$R^3$ is $CH_3-(CH_2)_q-CH(OH)_r-C(O)-O^{\ominus}$;

r is 0 or 1;

q is an integer ranging from 0 to 44;

Q is $-(CH_2)_a-$;

a is an integer ranging from 3 to 17;

A is either $-R$ or $-Q-C(O)-R^1$;

m is an integer ranging from 1 to 200;

n is an integer ranging from 1 to 10.

5. A compound of claim 4 wherein q is 0 and r is 0.

6. A compound of claim 4 wherein q is 1 and r is 0.

7. A compound of claim 4 wherein q is 0 and r is 1.

8. A compound of claim 4 wherein q is 1 and r is 1.

9. A compound of claim 4 wherein q is 6 and r is 0.

10. A compound of claim 4 wherein q is 8 and r is 0.

11. A compound of claim 4 wherein q is 10 and r is 0.

12. A compound of claim 4 wherein q is 12 and r is 0.

13. A compound of claim 4 wherein q is 14 and r is 0.

14. A compound of claim 4 wherein q is 16 and r is 0.

15. A compound of claim 4 wherein q is 18 and r is 0.

16. A compound of claim 4 wherein q is 20 and r is 0.

17. A compound of claim 4 wherein q is 44 and r is 0.

* * * * *